US012235678B2

(12) United States Patent
Belluco

(10) Patent No.: US 12,235,678 B2
(45) Date of Patent: Feb. 25, 2025

(54) SYSTEM AND METHOD FOR CONTROLLING AN INTERACTION BETWEEN AN OPERATOR AND A MACHINE

(71) Applicant: LWT3 S.R.L., Milan (IT)

(72) Inventor: Paolo Belluco, Milan (IT)

(73) Assignee: LWT3 S.R.L., Milan (IT)

( * ) Notice: Subject to any disclaimer, the term of this patent is extended or adjusted under 35 U.S.C. 154(b) by 0 days.

(21) Appl. No.: 17/907,085

(22) PCT Filed: Mar. 23, 2021

(86) PCT No.: PCT/IB2021/052385
§ 371 (c)(1),
(2) Date: Sep. 22, 2022

(87) PCT Pub. No.: WO2021/191784
PCT Pub. Date: Sep. 30, 2021

(65) Prior Publication Data
US 2024/0231429 A1    Jul. 11, 2024

(30) Foreign Application Priority Data

Mar. 24, 2020    (IT) .................. 102020000006238

(51) Int. Cl.
*G06F 1/16* (2006.01)
*B25J 9/00* (2006.01)
(Continued)

(52) U.S. Cl.
CPC ............. *G06F 1/163* (2013.01); *B25J 9/16* (2013.01); *B25J 13/08* (2013.01); *B25J 19/02* (2013.01); *G06F 3/011* (2013.01); *B25J 9/0006* (2013.01)

(58) Field of Classification Search
CPC ... B25J 9/1694; B25J 9/16; B25J 13/08; B25J 19/02; G06F 1/163; G06F 3/011
See application file for complete search history.

(56) References Cited

U.S. PATENT DOCUMENTS

| 6,002,957 A | 12/1999 | Finneran |
| 2015/0134080 A1* | 5/2015 | Roh ................. B25J 9/1694 |
| | | 623/32 |

(Continued)

FOREIGN PATENT DOCUMENTS

| EP | 1531726 A1 | 5/2005 |
| WO | 2018042407 A1 | 3/2018 |
| WO | 2019211691 A1 | 11/2019 |

OTHER PUBLICATIONS

Patent Cooperation Treaty, International Search Report and Written Opinion for International Application No. PCT/IB2021/052385, mailed Jul. 15, 2021, 17 pages.

*Primary Examiner* — Ian Jen
*Assistant Examiner* — Renee LaRose
(74) *Attorney, Agent, or Firm* — Stetina Brunda Garred & Brucker

(57) ABSTRACT

System for controlling at least one interaction between an operator and a machine, which system comprises at least one wearable device which is suitable to be worn by an operator and is provided with one or more sensors comprising one or more surface electromyographic sensors, wherein the wearable device comprises at least one data acquisition system suitable to receive and aggregate the data received from the sensors, at least one data processing system suitable to process the data received from the sensors, at least one data storage system suitable to store the data received from the sensors and/or processed by the data processing system, as well as at least one data display system suitable to display the data received by the sensors and/or processed by the data processing system, wherein the system further comprises one or more sensors suitable to detect parameters or actions of a machine and at least one control subsystem suitable to manage the data received from the sensors of the wearable device and of the machine, wherein the control subsystem comprises at least one data hub module suitable to acquire and aggregate the received data, as well as at least one expert system suitable to analyse the data acquired and aggregated (Continued)

by the data hub module to generate control data according to at least one interaction pattern between operator and machine, wherein the control subsystem also comprises at least one data storage system suitable to store the received data and the results of the processing of these data, wherein said control data can be sent from the control subsystem to the wearable device and/or the machine to control actions of the operator and/or the machine.

The present description also relates to a method which can be carried out by means of said system.

15 Claims, 4 Drawing Sheets

(51) Int. Cl.
  *B25J 9/16* (2006.01)
  *B25J 13/08* (2006.01)
  *B25J 19/02* (2006.01)
  *G06F 3/01* (2006.01)

(56) References Cited

U.S. PATENT DOCUMENTS

| | | |
|---|---|---|
| 2015/0148619 A1 | 5/2015 | Berg et al. |
| 2017/0259428 A1 | 9/2017 | Assad et al. |
| 2019/0224841 A1* | 7/2019 | Ly ................. A61B 5/4504 |

* cited by examiner

SYSTEM AND METHOD FOR CONTROLLING AN INTERACTION BETWEEN AN OPERATOR AND A MACHINE

CROSS-REFERENCE TO RELATED APPLICATIONS

This application claims priority to PCT International Application No. PCT/IB2021/052385 filed on Mar. 23, 2021, which application claims priority to Italian Patent Application No. 102020000006238 filed on Mar. 24, 2020, the entire disclosures of which are expressly incorporated herein by reference.

STATEMENT RE: FEDERALLY SPONSORED RESEARCH/DEVELOPMENT

Not Applicable

BACKGROUND

Technical Field

The present disclosure relates to a system for controlling interactions between an operator and a machine. The present description also relates to a method which can be carried out by means of said system.

Background of the Description

EP 1531726, US 2015/0148619 A1, U.S. Pat. No. 6,002,957, US 2019/0224841 A1 and WO 2018/042407 A1 describe systems and methods that employ wearable devices for obtaining data on the efforts and movements of persons by means of sensors of different type, such as accelerometers, gyroscopes, electromyography, or vision sensors for the acquisition of motion and kinematics of the body.

However, in these known systems and methods the data obtained from the wearable devices do not allow you to control the interaction between an operator and a machine.

SUMMARY OF THE DESCRIPTION

Object of the present description is therefore to provide a system and a method which are free from said drawbacks. Said object is achieved with a system and a method, the main features of which are specified in the attached claims, to be considered an integral part of the present description.

Thanks to their particular architecture, the system and the method according to the present description overcome the limits of the prior art, so as to automatically provide data linked between the efforts and movements of the operator and the task he is performing, and then also in relation with the data also coming from at least one machine that the operator is using, such as position of the movable elements, torques generated by the actuators, speed, temperatures and other physical quantities that measure the state of the machine.

Thus, the system and the method allow to warn the operator of possible dangers to his health, in real time and/or on a long-term thanks to a particular batch analysis, and also to send control data to the actuators of the machine which is used or to other operators who are present, so as to improve even the complementary movements in the interaction between several operators and several machines.

Thanks to a particular control subsystem, the system and the method allow to acquire data, perform analyses on the received data, send control data to the wearable devices of the operators and to the connected machines, such as speed and/or torques of the actuators, display the results of the data processing also in real time and to store both the data and the results of the processing. The control subsystem preferably uses artificial intelligence techniques to perform inferences on the data and for creating and updating patterns regarding the optimization of efforts, movements and postures which are used, also tailored to the individual operator, during his specific work tasks and during the interaction with specific machines.

The structure of the system also allows the acquisition, analysis and display of data concerning the user, the machine and preferably also the environment in which they are, so as to further improve the quality of life of the operator and of the production processes in which he interacts with the machine.

The system components also allow to collect and store automatic learning patterns to guide the improvement of ergonomics, safety and collaboration during various tasks that involve physical stress, such as repetitive and/or heavy assembly line work, handling of goods, hospital care and so on.

The system and the method preferably employ an access management subsystem based on blockchain technology, which allows the creation and the secure management of a register of entities (machines and operators) that have accessed, read or modified the data exchanged by all the system components.

In particular, the control subsystem allows to warn and advise the specific operator on the best type of movement in order to preserve his health and to send control data to the machines to optimize their behaviour according to the specific operator and his specific state at that time, such as posture, fatigue, muscle stress, heart rate and other parameters acquired by the wearable device or by the external sensors.

For example, a robot interacting with an operator in an assembly task could change the speed or the torques of the actuators in the joints, or change its configuration, position and orientation in the space of the environment in which it interacts with the operator, to avoid dangerous situations or favour the correct posture of the operator and the correct positioning of the assembled components according to the operator's parameters detected at that moment by his wearable device.

The wearable device comprises surface electromyographic sensors and the method comprises a particular step of processing the data obtained from these specific sensors, which analyses them in the frequency domain, in order to improve the quality of the data obtained from the wearable device.

BRIEF DESCRIPTION OF THE DRAWINGS

Further advantages and characteristics of the system and the method according to the present description will become evident to those skilled in the art from the following detailed description of some embodiments, to be considered non-limiting examples of the claims, with reference to the attached drawings wherein:

EXEMPLARY EMBODIMENTS

Figure 1:
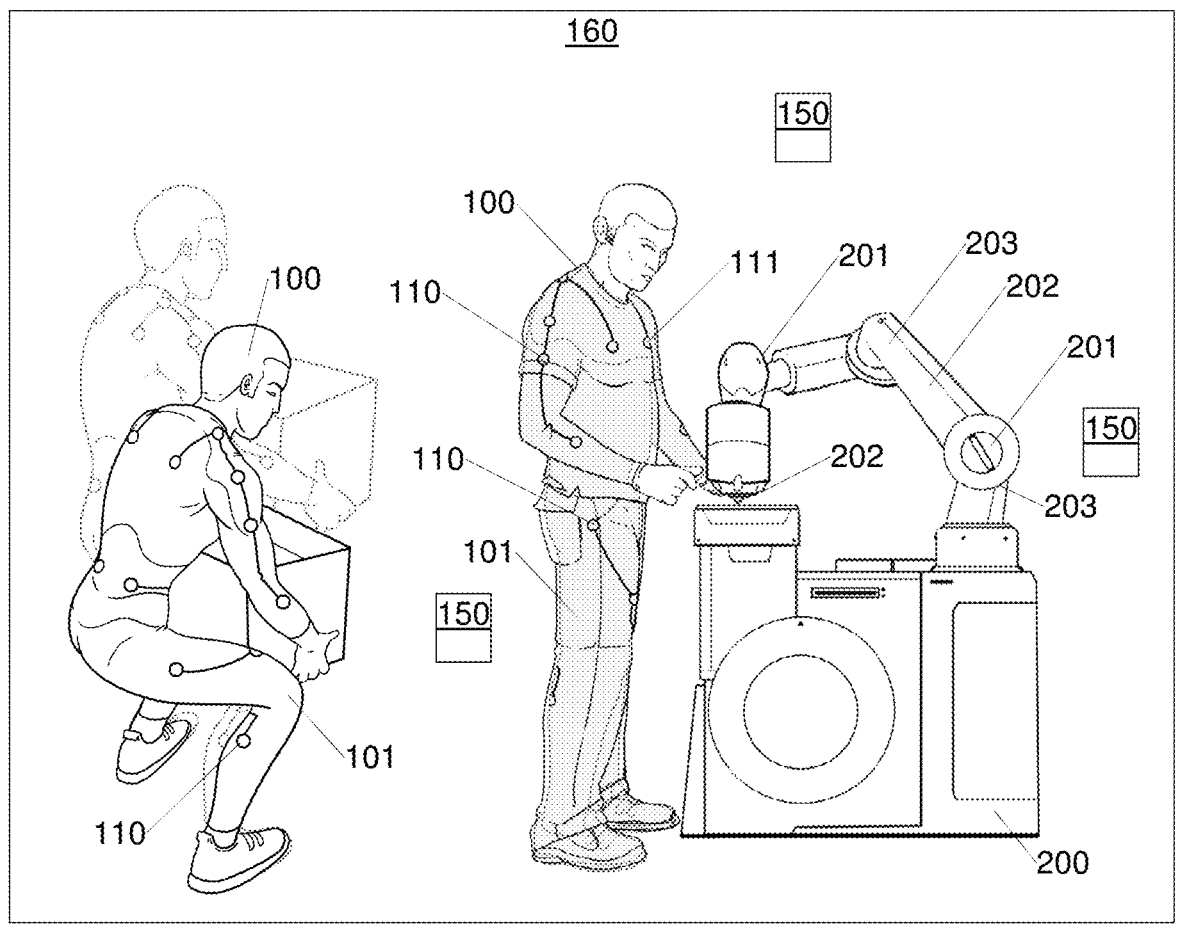
FIG. 1 shows an interaction between operator and machine.
Figure 2:
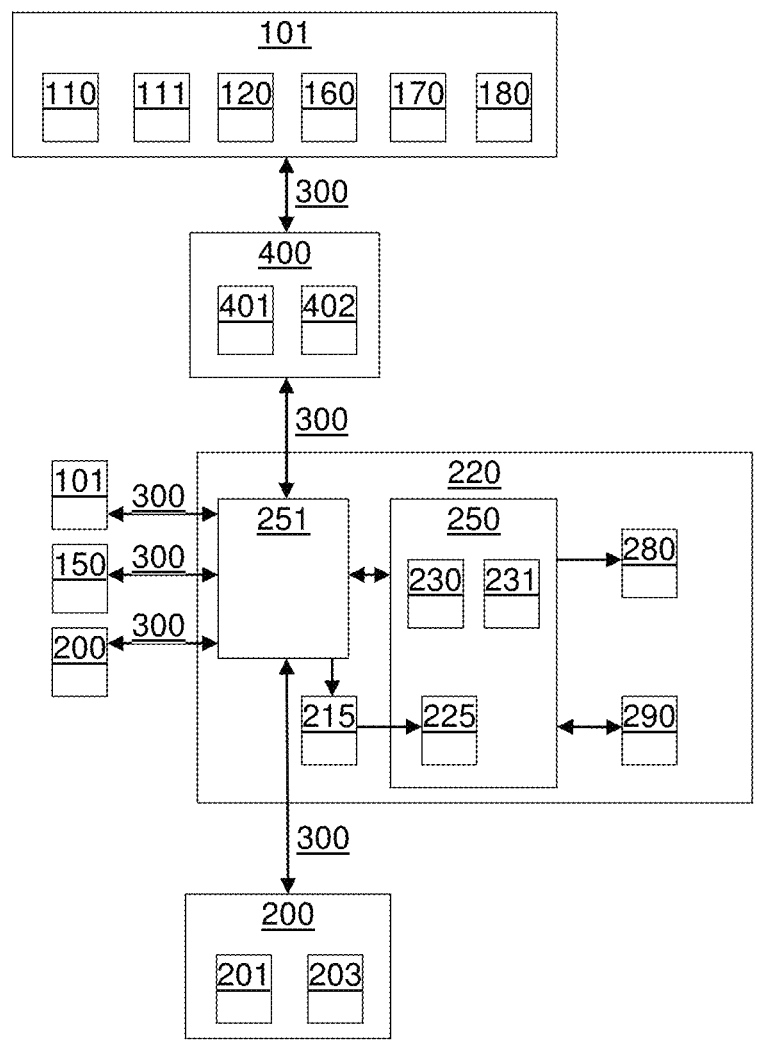
FIG. 2 is a scheme of an embodiment of the system.

As shown in FIGS. 1 and 2, at least one operator 100, for example a human being, may wear at least one wearable device 101, for example a suit, which is provided with one or more surface electromyographic sensors 110 suitable to measure the muscular activity of the operator 100 during his interaction with at least one machine 200, for example a robot. The machine 200 can be provided with one or more actuators 201, for example electric or hydraulic motors, and with one or more moving elements 202, for example the working head and/or arm portions of the robot, that are driven by actuators 201. The machine 200 further comprises one or more sensors 203 suitable for detecting parameters or actions of the actuators 201 and/or of the moving elements 202. The sensors 203 may comprise sensors of position, torque, speed, temperature or other physical quantities of the machine 200, in particular of the actuators 201 and the moving elements 202.

The wearable device 101 may comprise one or more further sensors 111 suitable to measure further parameters or actions of the operator 100, for example heart rate, body temperature, blood pressure, respiration, sweating, as well as posture, speed and/or accelerations of the body or of the limbs of the operator 100. The further sensors 111 may include in particular inertial measurement sensors (IMU), accelerometers, gyroscopes, magnetometers, optical fibres, motion-tracking systems based both on active or passive markers and on structured light or flight-time cameras, thermographic cameras, sensors of temperature, humidity, sound frequency and intensity, intensity of electromagnetic radiation, biometric sensors of heart rate, galvanic skin response, hydration, blood glucose, lactic acid and other biosensors, step counters and/or GPS-based geolocation systems, cellular networks (3G, 4G, 5G and any subsequent ones) radio frequency (Bluetooth, Wi-Fi, NFC, LoRaWan or others) and/or optical systems.

The wearable device 101 may further comprise at least one data acquisition system 120 suitable to receive and aggregate the data received from the sensors 110, 111, at least one data processing system 170 suitable to process the data received from the sensors 110, 111, at least one data storage system 160 suitable to store the data received from the sensors 110, 111 and/or processed by the data processing system 170, as well as at least one data display system 180 suitable to display the data received from the sensors 110, 111 and/or processed by the data processing system 170.

One or more external sensors 150, such as for example pressure, sound, light, temperature or movement sensors, may be arranged in an environment 160 outside the machine 200 to detect movements of the operator 100, the machine 200 or environmental conditions, as for example environmental noise, vibrations, air temperature or the lighting in the environment 160.

A further operator 100 provided with a further wearable device 101 may be present in the same environment 160 where the first operator 100 and the machine 200 are present. Further machines 200 provided with actuators 201 and sensors 203 may also be present in the environment 160.

The system comprises at least one control subsystem 220 suitable to manage the data received or transmitted by at least one wearable device 101 and by the sensors 203 of at least one machine 200, as well as by further wearable devices 101, further sensors 203 and/or the external sensors 150, if present. The control subsystem 220 comprises in particular a data hub module 251 suitable to acquire and aggregate data transmitted by the wearable devices 101, by the sensors 203 of the machines 200 and/or by sensors external 150, as well as at least one expert system 250 suitable to analyse the data acquired by the data hub module 251, in particular by means of a real-time analysis component 230 and/or a batch analysis component 225.

The real-time analysis component 230 of the expert system 250 analyses the received data in real time and generates real-time control data, in particular warnings, alarms, information, instructions and/or commands, based on at least one interaction pattern between operator and machine, previously elaborated. Control data can be sent by the expert system 250 of the control subsystem 220 to the wearable device 101 to send alerts and signals to the operator 100 through the data display system 180, to the actuators 203 of the machine 200 and/or to the external sensors 150 monitoring the environment 160, for controlling the actions of the operator 100 and/or the machine 200.

In particular, the batch analysis component 225 employs artificial intelligence techniques (machine learning tools, such as deep artificial neural networks, pattern recognition techniques, and other known methods of supervised, unsupervised or mixed learning) which, by using the received data and interaction patterns between operator and machine stored in the control subsystem 220, allow to process control data for the wearable device 101 and/or the machine 200.

The expert system 250 may also include a sending system 231 suitable to send said control data to the wearable device 101 and/or to the machine 200 through the data hub module 251.

The control subsystem 220 may also comprise at least one data storage system 215 capable of storing the received data and the results of the processing of these data, and/or at least one data display system 280 suitable to display said data and/or results.

The data display system 180, 280 of the wearable device 101 and/or of the control subsystem 220 is suitable to output data in the format of text, tables, charts, diagrams, images, sounds and/or vibrations, and includes one or more devices suitable to represent these formats, such as for example desktop computer, laptop, tablet, handheld PC, smartphone, smartwatch, smartglasses, wearable computer, embedded systems or other similar electronic devices including output means.

The control subsystem 220 may also comprise a knowledge base 290 suitable to store the interaction patterns between operator and machine which have been generated and used by the expert system 250 to generate the control data.

The system may comprise at least one access management subsystem 400 suitable to manage access, reading and editing of the data acquired by the wearable device 101, by the machine 200 and/or by the control subsystem 220. The access management subsystem 400 may be arranged at various points in the environment 160, also on a wearable device 101 or on the machine 200, or elsewhere, and/or preferably employs a blockchain technology comprising a blockchain register 401 of the operators 100 and the machines 200 that have accessed, read or modified the data transmitted and received, and/or an access management component 402 to manage the accesses to the system on the basis of the blockchain register 401. The blockchain register 401 is in particular a distributed register that is based on blockchain technology and contains a shared and immutable data structure, wherein the register data are grouped into blocks and concatenated in chronological order. The integrity of said concatenation and of the blockchain register 401 is guaranteed by cryptographic algorithms.

The system comprises one or more of apparatuses 300 suitable to transmit data to and/or from the wearable devices 101, the external sensors 150, the machine 200, the control subsystem 220 and/or the access management subsystem 400. The apparatuses 300 may comprise wired or wireless connections, in particular local data networks, geographic data networks or cloud platforms.

Figure 3:
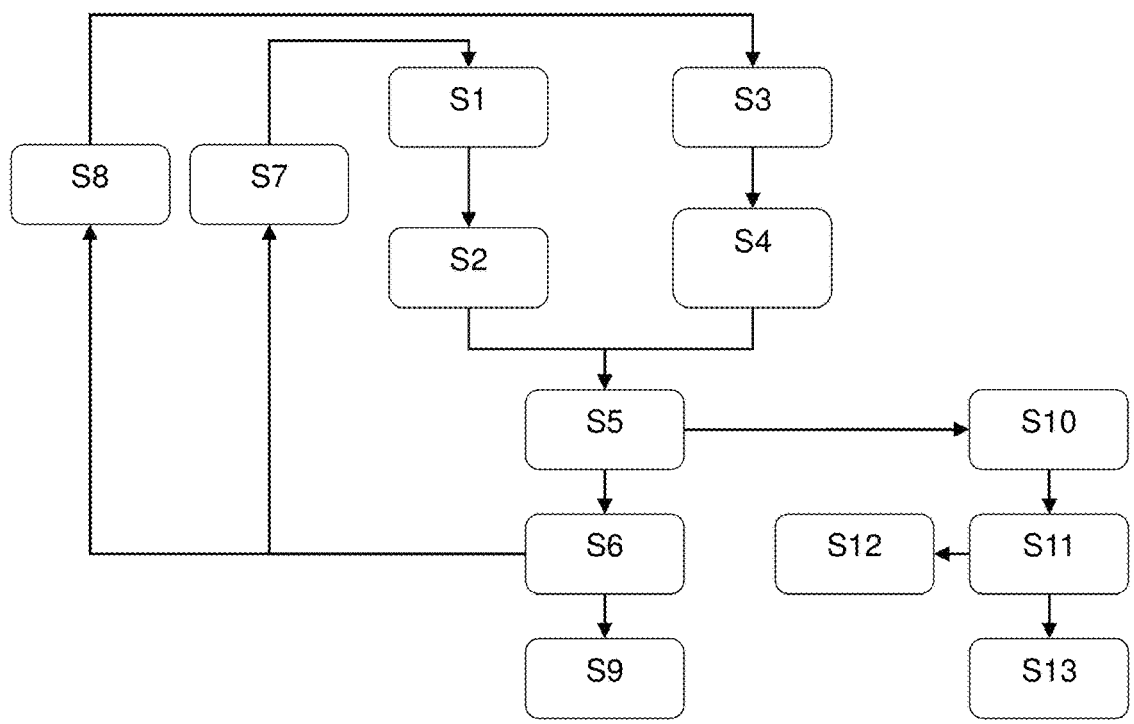
FIG. 3 is a flowchart of an embodiment of the method.

FIG. 3 shows a first step S1 of the method according to an embodiment, in which the operator 100 interacts with the machine 200 and a second step S2 in which the sensors 110 and 111 of the wearable device 101 of the operator 100 transmit data to the control subsystem 220. In the meantime, the machine 200 in a step S3 is operating with the actuators 201 and the moving elements 202, so that in a step S4 the sensors 203 of the machine 200 and any external sensors 150 in the environment 160 transmit data to the control subsystem 220.

In a step S5 the data hub module 251 captures and aggregates data transmitted by the wearable device 101, by the machine 200 and/or by the external sensors 150, after which in a step S6 the real-time analysis component 230 analyses the received data and generates control data which are sent in real time through the sending system 231 and the data hub module 251 to the wearable device 101 in a step S7 and/or to the actuators 201 of the machine 200 in a step S8. Information corresponding to this control data and/or other results obtained by the real-time analysis component 230 may be displayed by the data display system 280 in a step S9.

The data managed by the data hub module 251 can be stored in the data storage system 215 in a step S10, so that they can then be analysed by the batch analysis component 225 in a step S11 to update the knowledge base 290 in a step S12 and/or to create a report in a step S13.

Figure 4:
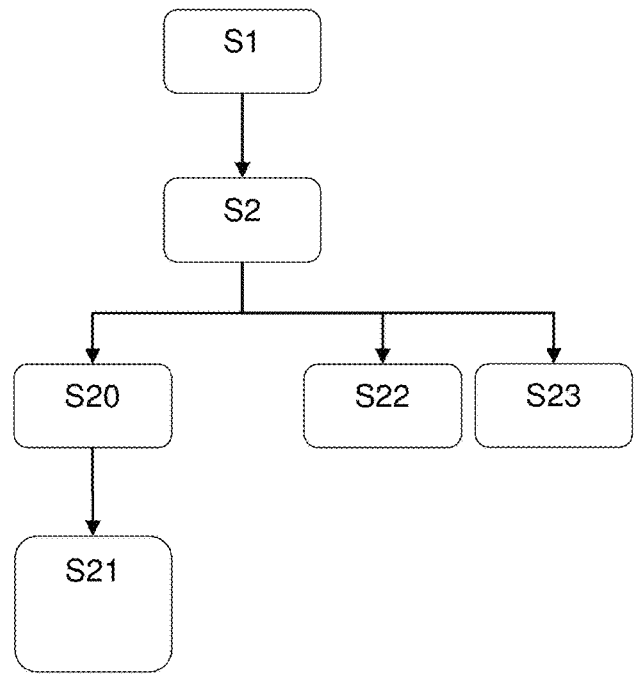
FIG. 4 is a flowchart of a variation of the method.

FIG. 4 shows a first step S1 and a second step S2 of the method according to a variation of the above-mentioned embodiment, which steps correspond to those described above. However, in a step S20 the data obtained by the sensors 110, 111 are processed by the data processing system 170, which sends control data to the operator 100 by means of the data display system 180 in a step S21. In a step S22 the data obtained by the sensors 110, 111 can be stored in the data storage system 160 of the wearable device 101. In a step S23 the data obtained by the sensors 110, 111 can be sent to the data hub module 251 to carry out the steps of the method described above, starting from step S5.

Figure 5:
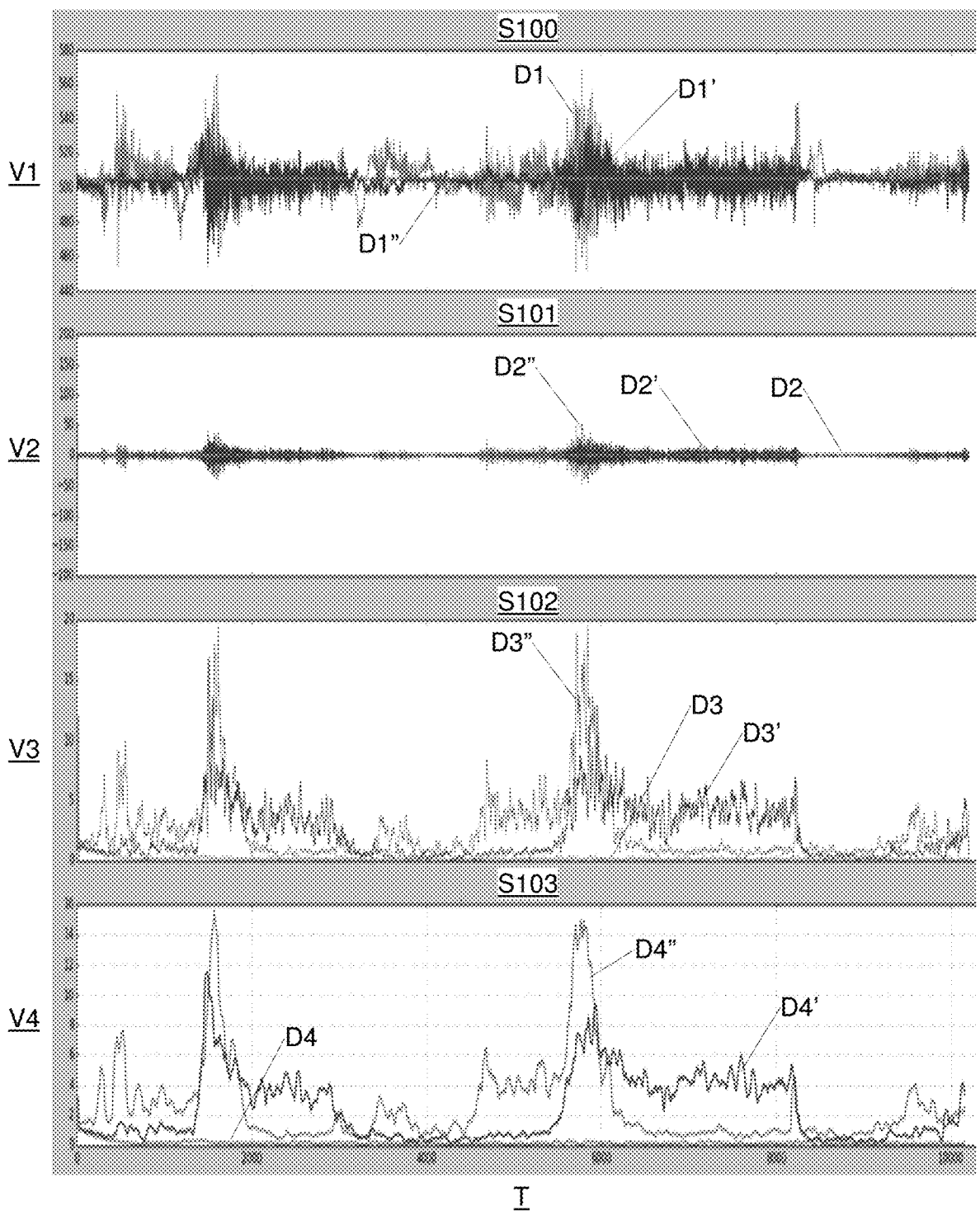
FIG. 5 shows a data processing step in the method.

FIG. 5 shows the results of the data analysis steps obtained by three electromyographic sensors 110 of three different muscle groups of the operator 100.

In a first step S100 carried out in a period of time T indicated in milliseconds, in particular during the aforementioned step S6, the raw data D1 (light grey), D1' (dark grey) and D1" (medium grey) of three sensors 110 are acquired simultaneously by the real-time analysis component 230. The values V1 of these raw data D1, D1', D1" can for example correspond to the voltage in mV or to the current in mA of an electrical signal generated by each sensor 110.

In a second step S101 the raw data D1, D1' and D1" are filtered by the real-time analysis component 230 to obtain filtered data D2, D2' and D2" with values V2. Filtering is for example obtained with a bandpass filter, in particular a third order Butterworth filter (lowcut 40, highcut 134.9).

In a third step S102 the filtered data D2, D2' and D2" are smoothed by the real-time analysis component 230, for example by means of a Savitzky-Golay filter, to obtain smoothed data D3, D3' and D3" with values V3.

In a fourth step S103 the smoothed data D3, D3' and D3" are processed by the real-time analysis component 230 to obtain root mean square values D4, D4' and D4" with values V4, which are then used for further data processing in the system and method according to the present description.

Variations or additions may be made by those skilled in the art to the embodiments described and illustrated here, while remaining within the scope of the following claims. In particular, further embodiments may comprise the technical features of one of the following claims with the addition of one or more technical features described in the text or illustrated in the drawings, taken individually or in any mutual combination.

The invention claimed is:

1. System for controlling at least one interaction between at least one operator and at least one machine provided with one or more actuators and with one or more moving elements that are driven by actuators, wherein the actions of the actuators can be controlled by means of control data, wherein said system comprises at least one wearable device which:
   a. is suitable to be worn by the operator,
   b. is provided with one or more sensors comprising one or more surface electromyographic sensors suitable to measure the muscular activity of the operator during his interaction with the machine,
   c. comprises at least one data acquisition system suitable to receive and aggregate the data received from the sensors,
   d. comprises at least one data processing system suitable to process the data received from the sensors,
   e. comprises at least one data storage system suitable to store the data received from the sensors and/or processed by the data processing system,
   f. comprises at least one data display system suitable to display the data received by the sensors and/or processed by the data processing system,
   wherein the system further comprises:
   g. one or more sensors suitable to detect parameters or actions of one or more of said actuators of the at least one machine and/or of one or more of said moving elements driven by the actuators,
   h. at least one control subsystem suitable to manage the data received from the sensors of the wearable device and of the machine, wherein the control subsystem comprises:
      h1. at least one data hub module suitable to acquire and aggregate the received data, and
      h2. at least one data storage system suitable to store the received data and the results of the processing of these data,
   wherein the control subsystem also comprises at least one expert system suitable to analyse the data acquired and aggregated by the data hub module to generate control data according to at least one interaction pattern between operator and machine, which interaction pattern is stored in the control subsystem, wherein the control subsystem is suitable to send said control data to the data display system of the wearable device and to the actuator(s) of the machine to control actions of the operator and of the machine.

2. The system according to claim 1, wherein the wearable device comprises one or more sensors which are suitable to measure parameters or actions of the operator and are chosen among: inertial measurement sensors (IMU), accelerometers, gyroscopes, magnetometers, optical fibres, motion-tracking systems based both on active or passive markers and on structured light or flight-time cameras, thermographic cameras, sensors of temperature, humidity, sound frequency and intensity, intensity of electromagnetic radiation, biometric sensors of heart rate, galvanic skin response, hydration, blood glucose, lactic acid and other biosensors, step counters and/or GPS-based geolocation systems, cellular networks (3G, 4G, 5G and any subsequent ones), radio frequency (Bluetooth, Wi-Fi, NFC, LoRaWan or others) and/or optical systems.

3. The system according to claim 1, wherein the control subsystem also comprises at least one data display system suitable to display said data and/or said results.

4. The system according to claim 1, wherein the data display system of the wearable device and/or of the control subsystem comprises one or more devices suitable to output data in the format of text, tables, graphs, diagrams, images, sounds and/or vibrations.

5. The system according to claim 1, wherein the expert system comprises a real-time analysis component and/or a batch analysis component.

6. The system according to claim 5, wherein the batch analysis component is suitable to process with artificial intelligence techniques the received data and interaction patterns between operator and machine stored in the control subsystem to generate the control data for the wearable device and/or to the machine.

7. The system according to claim 1, wherein the control subsystem also comprises a knowledge base suitable to store interaction patterns between operator and machine, which have been generated and used by the expert system to generate the control data.

8. The system according to claim 1, wherein the system comprises at least one access management subsystem suitable to manage access, reading and modification of the data acquired by the wearable device, by the machine and/or by the control subsystem, wherein the access management subsystem comprises a blockchain register of one or more operators and of one or more machines that have accessed, read or modified the data transmitted and received, as well as an access management component to manage accesses to the system according to the blockchain register.

9. The system according to claim 1, wherein the system comprises one or more external sensors suitable to be arranged in an environment outside the machine to detect movements of the operator, the machine and/or conditions in the environment, wherein the control subsystem is suitable to manage also the data received from the external sensors for generating the control data for the wearable device and/or for the machine.

10. Method for controlling at least one interaction between at least one operator and at least one machine provided with one or more actuators and with one or more moving elements that are driven by actuators, wherein the actions of the actuators can be controlled by means of control data, which comprises the following steps:
one or more sensors, suitable to detect parameters or actions of one or more of said actuators of the machine and/or of one or more of said moving elements driven by the actuators, are applied to the machine;
the operator wears a wearable device which is provided with one or more sensors comprising one or more surface electromyographic sensors suitable to measure the muscular activity of the operator during his interaction with the machine, wherein the wearable device comprises at least one data acquisition system suitable to receive and aggregate the data received from the sensors, at least one data processing system suitable to process the data received from the sensors, at least one data storage system suitable to store the data received from the sensors and/or processed by the data processing system, as well as at least one data display system suitable to display the data received from the sensors and/or processed by the data processing system;
the sensors of the wearable device and of the machine transmit data to a control subsystem which receives and manages this data, wherein the control subsystem includes a data hub module suitable to acquire and aggregate the data received, a data storage system suitable to store at least the data received, as well as at least one expert system suitable to analyse the data acquired and aggregated by the data hub module;
the control subsystem generates control data according to at least one interaction pattern between operator and machine, which interaction pattern is stored in the control subsystem;
the control subsystem sends said control data to the data display system of the wearable device and to the actuator(s) of the machine to control actions of the operator and of the machine.

11. The method according to claim 10, wherein the expert system processes with artificial intelligence techniques the received data and interaction patterns between operator and machine stored in the control subsystem to generate the control data for the wearable device and/or for the machine.

12. The method according to claim 10, which comprises the following further steps:
one or more external sensors are arranged in an environment outside the machine to detect movements of the operator, the machine and/or conditions of the environment;
the control subsystem manages also the data received from the external sensors;
the control subsystem generates the control data also according to the data received from the external sensors.

13. The method according to claim 10, wherein at least one access management subsystem manages access, reading and modification of the data acquired by the wearable device, by the machine and/or by the control subsystem, wherein the access management subsystem comprises at least one blockchain register of one or more operators and of one or more machines that have accessed, read or modified the data transmitted and received, as well as at least one access management component to manage accesses to the system according to the blockchain register.

14. The method according to claim 10, wherein the analysis of the data of the surface electromyographic sensors comprises the following steps:
the raw data of the sensors are filtered in the frequency domain to obtain filtered data;
said filtered data are smoothed;
said smoothed data are processed to obtain root mean square values of the data.

15. The method according to claim 10, wherein the steps are carried out by a system according to claim 1.

* * * * *